(12) United States Patent
Montgomery

(10) Patent No.: US 9,033,894 B2
(45) Date of Patent: May 19, 2015

(54) SYSTEM FOR REMOTE COMMUNICATION OF HEARTBEAT

(75) Inventor: Joanna Montgomery, South Queensferry (GB)

(73) Assignee: Little Riot Ltd., South Queensferry (GB)

( * ) Notice: Subject to any disclaimer, the term of this patent is extended or adjusted under 35 U.S.C. 154(b) by 0 days.

(21) Appl. No.: 14/115,350

(22) PCT Filed: May 3, 2012

(86) PCT No.: PCT/GB2012/050968
§ 371 (c)(1),
(2), (4) Date: Nov. 12, 2013

(87) PCT Pub. No.: WO2012/150457
PCT Pub. Date: Nov. 8, 2012

(65) Prior Publication Data
US 2014/0088448 A1     Mar. 27, 2014

(30) Foreign Application Priority Data

May 3, 2011    (GB) .................................. 1107255.0

(51) Int. Cl.
*A61B 5/02*       (2006.01)
*A61B 5/04*       (2006.01)
(Continued)

(52) U.S. Cl.
CPC ............. *A61B 5/0004* (2013.01); *A61B 5/6826* (2013.01); *A61B 5/7405* (2013.01);
(Continued)

(58) Field of Classification Search
USPC ..................... 600/508–509; 607/60
See application file for complete search history.

(56) References Cited

U.S. PATENT DOCUMENTS

| | | |
|---|---|---|
| 2002/0019584 A1 | 2/2002 | Schulze |
| 2003/0102983 A1 | 6/2003 | Hung |

(Continued)

FOREIGN PATENT DOCUMENTS

| | | |
|---|---|---|
| KR | 1020040020597 A | 3/2004 |
| WO | 98/17172 A2 | 4/1998 |

(Continued)

OTHER PUBLICATIONS

Julia Werner, Reto Wettach, Eva Hornecker: "United-Pulse: Feeling Your Partner's Pulse", Sep. 2, 2008, Amsterdam. Retrieved from the Internet: URL:http://www.lehornecker.de/papers/dm004-werner.pdf [retrieved on Oct. 19, 2012].
International Search Report of related PCT App. No. PCT/GB2012/050968, Feb. 1, 2015.

*Primary Examiner* — Nicole F Lavert
(74) *Attorney, Agent, or Firm* — Benesch, Friedlander, Coplan & Aronoff, LLP; Thomas Y. Kendrick

(57) ABSTRACT

A system for remote communication of physiological information from one person to another and, more particularly, the mutual communication of heartbeat between two persons. The system comprises a web server which cooperates with two remote installations identified as A and B. Each of the remote installations comprises a heartbeat sensor, a pillow, and a local host. The local host may be a personal computer or laptop, or a suitable mobile phone running an appropriate application. The heartbeat sensor monitors the heartbeat of person A which is communicated via their pillow, their local host and a server, and then via a second local host to produce a visual and audible representation of heartbeat A in a pillow located with person B. At the same time, the heartbeat of person B is represented in the same manner at the pillow of person A.

16 Claims, 2 Drawing Sheets

(51) Int. Cl.
*A61N 1/00* (2006.01)
*A61B 5/00* (2006.01)
*A61B 5/024* (2006.01)
*G06F 19/00* (2011.01)
*G06Q 50/22* (2012.01)
*H04L 29/08* (2006.01)

(52) U.S. Cl.
CPC ............. *A61B5/7455* (2013.01); *A61B 5/7465* (2013.01); *A61B 5/0022* (2013.01); *A61B 5/02438* (2013.01); *G06F 19/3418* (2013.01); *G06Q 50/22* (2013.01); *H04L 67/025* (2013.01); *H04L 67/125* (2013.01); *A61B 5/024* (2013.01); *A61B 5/6891* (2013.01); *A61B 5/742* (2013.01)

(56) References Cited

U.S. PATENT DOCUMENTS

2009/0018454 A1    1/2009  Hung
2009/0328130 A1*  12/2009  Hamilton et al. ................ 726/1

FOREIGN PATENT DOCUMENTS

| WO | 2006/063341 | A2 | 6/2006 |
| WO | 2006/090371 | A2 | 8/2006 |
| WO | 2009/112972 | A2 | 9/2009 |
| WO | 2010/111651 | A1 | 9/2010 |
| WO | 01/89362    | A2 | 11/2011 |

* cited by examiner

US 9,033,894 B2

SYSTEM FOR REMOTE COMMUNICATION OF HEARTBEAT

CROSS-REFERENCE TO RELATED APPLICATIONS

This application is a National stage entry under 35 U.S.C. §371 of PCT Patent Application No. PCT/GB2012/050968, filed May 3, 2012, which claims priority to United Kingdom Patent Application No. GB 1107255.0, filed on May 3, 2011, each of which is hereby incorporated by reference.

FIELD OF THE INVENTION

This invention relates to a system for remote communication of physiological information from one person to another, and more particularly the mutual communication of heartbeat between two persons; and to related methods and products.

BACKGROUND OF THE INVENTION

Modern technology has enabled a vast increase in the ability to communicate remotely, as by landline and mobile telephone, and Internet enabled services such as email and VOIP. However, all of these are essentially based on written or verbal communication. The present invention arose from a desire to utilise technology to bring people together in a more intimate way. When partners are geographically separated, they have an emotional need not only to communicate by voice or script, but also by continuing some feeling of physical proximity and intimacy.

The present invention addresses this need.

SUMMARY OF THE INVENTION

Accordingly the present invention in one aspect provides a system for remote communication of heartbeat; the system comprising:
- a heartbeat sensor module attachable to a subject, the heartbeat sensor module having a heartbeat sensor operating to produce a signal representing the heartbeat of the subject and a wireless communication transmitter for communicating said heartbeat signal;
- a host device located in proximity to the subject, the host device including a wireless communication receiver for receiving said heartbeat signal, and including data transfer means for communicating said signal over a data network;
- a server connected to the data network to receive said signal and to communicate it to an authorised destination host device;
- a destination host device connected to the data network to receive said signal when authorised;
- an output device for producing a visual and/or audible representation of the source heartbeat.

In a particularly preferred form of the system, the source includes an output device and the destination includes a heartbeat sensor module, whereby heartbeat signals are mutually exchanged between two subjects.

Preferably, each of the output devices comprises a loudspeaker and/or a light source optionally for locating within a pillow or pillow covering.

The output device may be in the form of a pillow or pillow covering comprising a loudspeaker and/or a light source.

Preferably also, the heartbeat sensor module (or each of the heartbeat sensor modules) is in the form of a finger ring.

Each heartbeat sensor module may communicate with its host device via its output device. Preferably each heartbeat sensor module communicates with its output device via ISM radio, and each output device communicates with its host device via Bluetooth.

Each output device preferably has a unique ID, and each heartbeat sensor module after powering up locks to the ID of a given output device.

From another aspect, the present invention provides a heartbeat sensor module for use in the foregoing system, comprising a heartbeat sensor operating to produce a signal representing the heartbeat of the subject and a wireless communication transmitter for communicating said heartbeat signal; the module being in the form of a finger ring.

The heartbeat sensor module may include means for locking to the unique ID of a given output device.

The invention further provides an output device for use in the above system, comprising a visual and/or audible output unit for locating within a pillow or pillow covering.

The output device may be in the form of a pillow having a pillow covering and a resilient filling, and further comprising a visual and/or audible output unit located within the pillow or pillow covering.

The output unit preferably comprises a loudspeaker and one or more LEDs.

The output device may include means for storing a unique ID and for transmitting the unique ID to an associated heart sensor module.

Another aspect of the present invention provides a method of providing non-verbal communication between two persons, A and B, who are geographically remote, the method comprising monitoring A's heartbeat and communicating that heartbeat to B aurally and/or visually, and simultaneously monitoring B's heartbeat and communicating that heartbeat to A aurally and/or visually.

The communication is preferably effected via a web server.

BRIEF DESCRIPTION OF THE DRAWINGS

An embodiment of the present invention will now be described, by way of example only, with reference to the drawings, in which.

DETAILED DESCRIPTION

Figure 1:
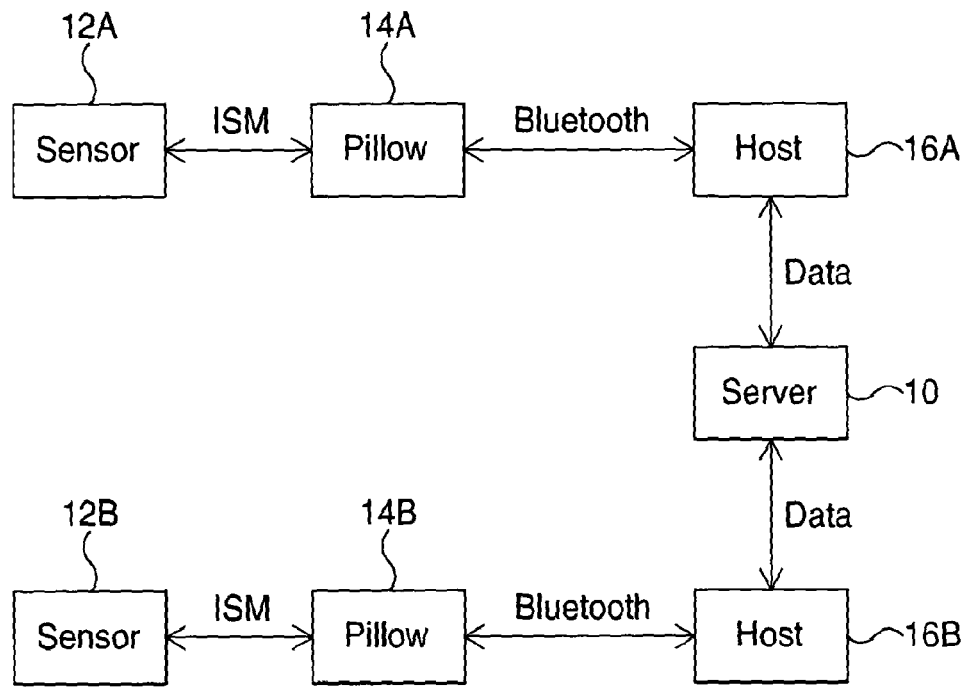
FIG. 1 is a schematic block diagram of a system forming one embodiment of the invention.
Figure 2:
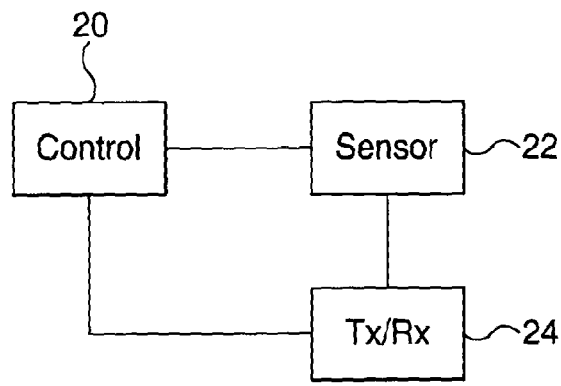
FIG. 2 shows a heartbeat sensor module of FIG. 1 in more detail.

Referring to FIG. 1, the system comprises a web server 10 which cooperates with two remote installations identified as A and B. Each of the remote installations comprises a heartbeat sensor 12, a pillow 14, and a local host 16. The host 16 may be a personal computer or laptop, or a suitable mobile phone running an appropriate application.

In outline, the heartbeat sensor 12A monitors the heartbeat of person A which is communicated via the pillow 14A, the host 16A and the server 10, and then via the host 16B to produce a visual and audible representation of heartbeat A in the pillow 14B. At the same time, the heartbeat of person B is represented in the same manner at the pillow 14A.

In this embodiment, communication between the heartbeat sensor 12 and its associated pillow 14 is by ISM radio, and between the pillow 14 and its associated host 16 is by Bluetooth. These are preferred for reasons of convenience and low power consumption, but alternatively any suitable link (preferably wireless) may be used; for example the link between pillow and host could be infrared.

Figure 3:
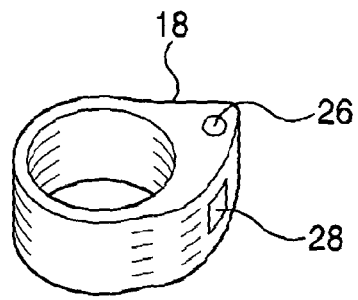
FIG. 3 is a perspective view of the heartbeat sensor module in the form of a ring.

In the present embodiment the heartbeat sensors 12 are in the form of finger rings as illustrated at 18 in FIG. 3. The ring 18 contains circuitry comprising a micro-controller 20, a heartbeat sensing unit 22, and a transceiver 24. A status LED 26 and on/off switch 28 may be provided on the ring 18. The sensing unit 22 may comprise a LED and light sensor which, as is known per se, detect heartbeat by detecting changes in blood density in the peripheral blood vessels as blood pressure changes under the action of the heart.

Figure 4:
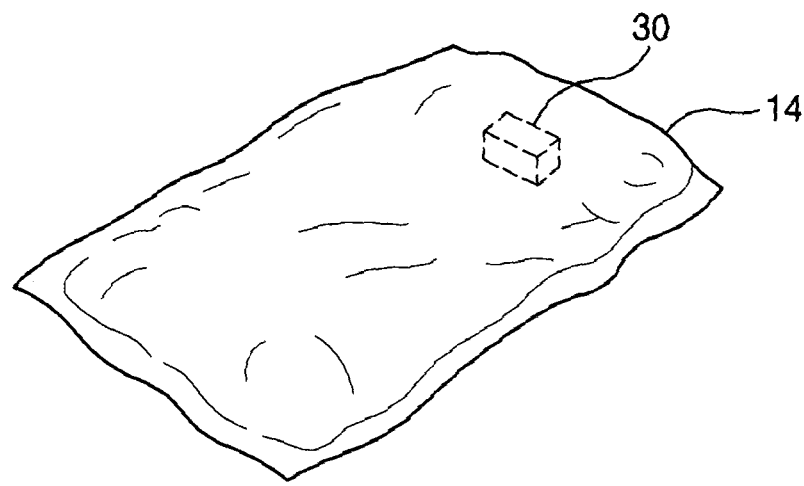
FIG. 4 shows an output device of FIG. 1 in the form of a pillow.
Figure 5:
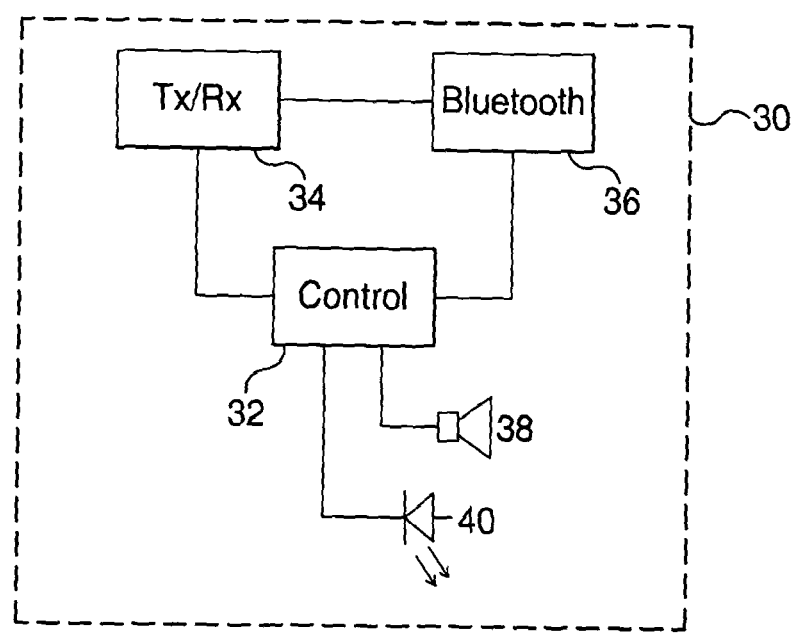
FIG. 5 shows circuitry contained in the pillow of FIG. 4 in more detail.

Turning to FIG. 4, the pillow 14 is largely a conventional pillow having a covering filled with resilient material such as polyester wadding. However, within the cover there is also positioned an output unit 30. As seen in FIG. 5, the output unit 30 comprises a micro-controller 32, an ISM transceiver 34, a Bluetooth transceiver 36, a loudspeaker 38, and one or more LEDs 40. The loudspeaker 38 and LEDs 40 are located in the output unit and within the pillow 14 so as to be audible to a person close to the pillow, and to give a visual glow through the pillow covering.

Once a ring 12 is switched on, the ring transceiver 24 broadcasts heart rate approximately every 2 seconds. A pillow that receives the transmission acknowledges it within 4 to 5 ms. Transmission is at 250 kbps using burst transfers. On receiving an acknowledgement, the ring 12 locks onto the ID of that pillow 14, and every heartbeat broadcast thereafter contains the ID of that pillow. This locking remains in place until the ring is power cycled. A pillow will only accept signals from an unlocked ring, or signals that contain its own ID. This enables multiple rings and pillows to be used in close proximity.

If the ring receives no acknowledgement, it will turn off after a pre-set time as a power saving measure.

The pillow 14 listens for packets from the ISM link and acknowledges as discussed above. If a Bluetooth connection to a host 16 exists, the heartbeat from the ring 12 is transmitted to the host 16.

The host 16 acts as a proxy between the Bluetooth connection and the web server 10, and provides the user with feedback about the pairing of two pillows. The host 16 connects to a pillow 14 using the Bluetooth connection; the pillow 14 is identified as an SSP device and appears as a virtual serial port on the host 16. Data rate is 115.2 kbps.

A standard HTTP protocol is used to transfer data between paired pillows. The web server 10 provides the wide area connection between two pillows. It maintains a list of pillow IDs and corresponding heart rates. There is no peer-to-peer connection between the two users; this is likely to be prohibited by many public (e.g. hotel) routers. The server 10 can be any standard HTTP server. It accepts HTTP requests to update records of pillow IDs and retrieve heart rates of paired pillows.

Each host 16 receives heartbeat data from its paired remote sensor. This is fed to the local pillow 14 and used to drive the loudspeaker 38 and LED 40.

Each host 16 has a front end application which graphically denotes the status of the local pillow and the remote pillow. A set-up screen is used to denote the paired pillow's ID and to adjust audio volume and LED brightness.

The output device may be in the form of a pillow unit, configured for placement around a pillow or within a pillow-case. Alternatively the output device may be designed to be held by or worn by a person, or could simply be designed to be placed on a bedside table, for example. As noted above, the heartbeat sensor module can communicate with its host device via its output device.

The unique ID for each pillow is assigned as follows. Each Bluetooth module has a unique ID. Both the phone (or other local hub) and the pillow unit enter Bluetooth search mode. The pillow unit then becomes identifiable on the phone, and thus visible to a user of the phone. The user then selects the pillow unit on the phone, and the devices are paired. Once paired, the phone will remember the unique ID and will automatically pair to the pillow unit when Bluetooth is on. If the user wishes to un-pair the phone from the pillow unit, they will select this option on the phone and re-pair to another pillow unit.

The features of the pillow unit (output device) and optionally the ring (heartbeat sensor) can be managed using bespoke software on, for example, the phone. This can be in the form of a programme or application (app) as are commonly used on "smart" phones.

In one arrangement, the pillow unit has two different coloured LEDs and once the devices are paired the phone will show the colour of the pillow unit. For example, the phone may show a blue link and a blue LED will show on the pillow unit to indicate they are paired.

Further modifications may be made to the foregoing embodiment within the scope of the present invention. For example:

The ring may communicate directly to the host rather than via the pillow.

Heartbeat detection may be effected by other means, such as electrical conductance on the chest, or acoustically by microphone.

Wireless communication other than ISM and Bluetooth may be used.

Although two-way communication of heartbeat is preferred, the invention in its broad aspect could be applied to one-way communication.

Whilst this invention has been described with reference to the sample embodiments thereof, it will be appreciated by those of ordinary skill in the art that modifications can be made to the structure and elements of the invention without departing from the spirit and scope of the invention as a whole.

What is claimed is:

1. A system for remote communication of a current source heartbeat, the system comprising:
   a first heartbeat sensor module attachable to a first subject, the first heartbeat sensor module having a heartbeat sensor operating repetitively to produce a signal representing the current source heartbeat of the first subject and a wireless communication transmitter for communicating the heartbeat signal;
   a host device located in proximity to the first subject, the host device including a wireless communication receiver for receiving the heartbeat signal, and including data transfer means for communicating the signal over a data network;
   a server connected to the data network to receive the signal and to communicate the signal to an authorized destination host device;
   a first destination host device connected to the data network to receive the signal when authorized;
   a first output device for producing at least one of a visual representation of the current source heartbeat and an audible representation of the current source heartbeat.

2. The system of claim 1, further comprising a second output device located in proximity to the first subject and a second heartbeat sensor module attachable to a second subject located in proximity to the first destination host device, whereby heartbeat signals are mutually exchanged between the first subject and the second subject.

3. The system of claim 2, wherein each of the first output devices and second output device comprises at least one of a loudspeaker for locating within a pillow or a pillow covering and a light source for locating within a pillow or a pillow covering.

4. The system of claim 2, wherein the first output device and second output device is in the form of a pillow, or a pillow covering, comprising a loudspeaker and/or a light source.

5. The system of claim 1, wherein the first heartbeat sensor module is in the form of a finger ring.

6. The system of claim 2, wherein each of the first heartbeat sensor module and the second heartbeat sensor module communicates with its host device via its output device.

7. The system of claim 6, wherein each of the first heartbeat sensor module and the second heartbeat sensor module communicates with its output device via ISM radio frequency, and each output device communicates with its host device via Bluetooth wireless technology standard.

8. The system of claim 6, wherein each of the first output device and the second output device has a unique ID, and wherein each of the first heartbeat sensor module and the second heartbeat sensor module after powering up locks to the ID of a given output device.

9. The system of claim 1, wherein the first heartbeat sensor module comprises a heartbeat sensor operating to produce a signal representing the current heartbeat of the first subject and a wireless communication transmitter for communicating the heartbeat signal; the module being in the form of a finger ring.

10. The system of claim 9, wherein the first heartbeat sensor module includes a means for locking to the unique ID of a given output device.

11. The system of claim 1, wherein the first output device comprises at least one of a visual output unit for locating within a pillow or a pillow covering and an audible output unit for locating within a pillow or a pillow covering.

12. The system of claim 11, wherein the first output device comprises a pillow having a pillow covering and a resilient filling, and wherein the first output device further comprises at least one of a visual output unit and an audible output unit.

13. The system of claim 11, wherein the output unit comprises a loudspeaker and one or more LEDs.

14. The system of claim 11, wherein the first output device includes a means for storing a unique ID and for transmitting the unique ID to an associated heart sensor module.

15. A method for providing a non-verbal communication between two persons, A and B, who are geographically remote from one another, the method comprising:
  monitoring person A's heartbeat and communicating that heartbeat to person B at least one of aurally and visually, and
  simultaneously monitoring person B's heartbeat and communicating that heartbeat to person A at least one of aurally and visually.

16. The method of claim 15, wherein the communication is effected via a web server.

* * * * *